US010779776B2

(12) United States Patent
Koehler et al.

(10) Patent No.: US 10,779,776 B2
(45) Date of Patent: Sep. 22, 2020

(54) APPARATUS FOR X-RAY IMAGING AN OBJECT

(71) Applicant: KONINKLIJKE PHILIPS N.V., Eindhoven (NL)

(72) Inventors: Thomas Koehler, Norderstedt (DE); Hanns-Ingo Maack, Norderstedt (DE); Thomas Pralow, Buchholz i.d.N. (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 159 days.

(21) Appl. No.: 15/779,107

(22) PCT Filed: Nov. 21, 2016

(86) PCT No.: PCT/EP2016/078224
§ 371 (c)(1),
(2) Date: May 25, 2018

(87) PCT Pub. No.: WO2017/093055
PCT Pub. Date: Jun. 8, 2017

(65) Prior Publication Data
US 2018/0344268 A1    Dec. 6, 2018

(30) Foreign Application Priority Data
Dec. 1, 2015 (EP) .................................... 15197268

(51) Int. Cl.
*A61B 6/00* (2006.01)
(52) U.S. Cl.
CPC ............ *A61B 6/405* (2013.01); *A61B 6/4035* (2013.01); *A61B 6/4291* (2013.01); *A61B 6/484* (2013.01);
(Continued)

(58) Field of Classification Search
CPC ..... A61B 6/4035; A61B 6/405; A61B 6/4291; A61B 6/484; A61B 6/488; A61B 6/5258; A61B 6/5294; A61B 6/542
See application file for complete search history.

(56) References Cited

U.S. PATENT DOCUMENTS

2012/0145912 A1    6/2012 Iwakiri
2013/0011040 A1    1/2013 Kido
(Continued)

FOREIGN PATENT DOCUMENTS

WO    WO2011068230 A1    6/2011
WO    WO2012057278 A1    3/2012
WO    WO2013004574 A1    1/2013

OTHER PUBLICATIONS

Liu Y ei al: "Recent Advances in Snchrotron-Based Hard X-Ray Phase Contrast Imaging", Journal of Physics D: Applied Physics, Institute of Physics Publishing Ltd, GB, vol. 45, No. 49, Nov. 22, 2013 (Nov. 22, 2013), p. 494001, XP020253615.
(Continued)

Primary Examiner — Marcus H Taningco
(74) Attorney, Agent, or Firm — Larry Liberchuk

(57) ABSTRACT

The present invention relates to an apparatus for X-ray imaging an object. It is described to provide (20) data relating to the detection of X-rays, wherein an X-ray detector is configured to be positioned relative to an X-ray source such that at least a part of a region between the X-ray source and the X-ray detector is an examination region for accommodating an object. An X-ray interferometer arrangement is configured to be positioned relative to the examination region. At least one X-ray dark field factor and at least one transmission factor are determined for the X-ray radiation transmitted through at least part of the object is determined. An intensity of X-ray radiation to be emitted towards the at least part of the object is controlled as a function of the
(Continued)

determined at least one dark field factor and the determined at least one transmission factor.

14 Claims, 5 Drawing Sheets

(52) U.S. Cl.
CPC ............ *A61B 6/5258* (2013.01); *A61B 6/542* (2013.01); *A61B 6/488* (2013.01); *A61B 6/5294* (2013.01)

(56) References Cited

U.S. PATENT DOCUMENTS

| | | | |
|---|---|---|---|
| 2014/0126690 A1* | 5/2014 | Yamaguchi ............ | A61B 6/484 378/36 |
| 2015/0031986 A1 | 1/2015 | Bernhardt | |
| 2015/0139383 A1* | 5/2015 | Proksa ................. | G01N 23/046 378/7 |
| 2016/0035450 A1* | 2/2016 | Date ...................... | G21K 1/067 378/36 |

OTHER PUBLICATIONS

Meinel, F. et al., "Improved Diagnosis of Pulmonary Emphysema Using In Vivo Dark-Field Radiography", Investigative Radiology, vol. 49, No. 10, pp. 653-657, Oct. 2014.
Weber, T. et al., "Noise in X-Ray Grating-Based Phase-Contrast Imaging", Medical Physics, vol. 38, No. 7, pp. 4133-4140, Jul. 2011.

* cited by examiner

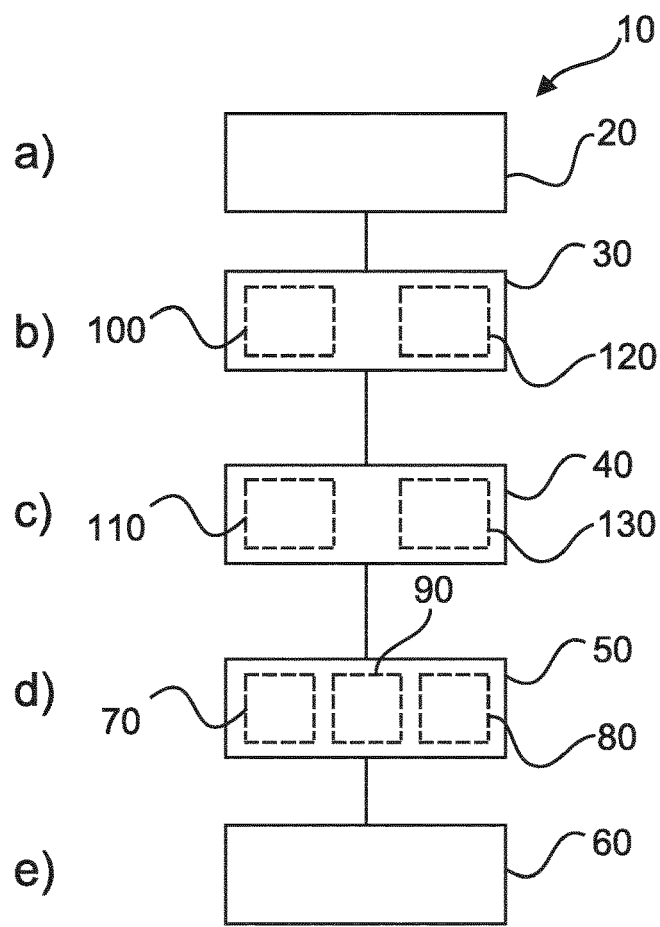
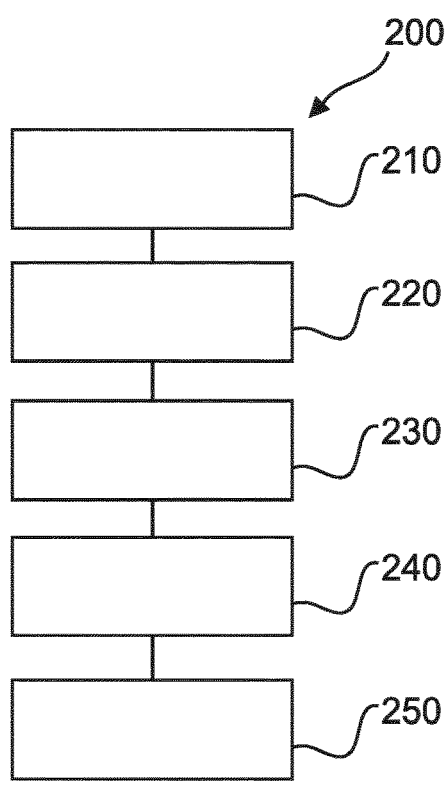

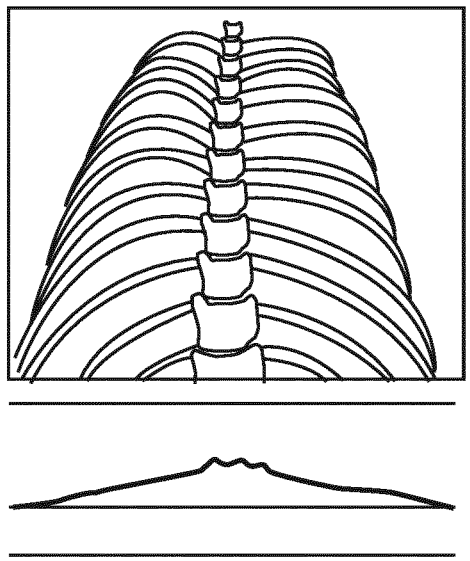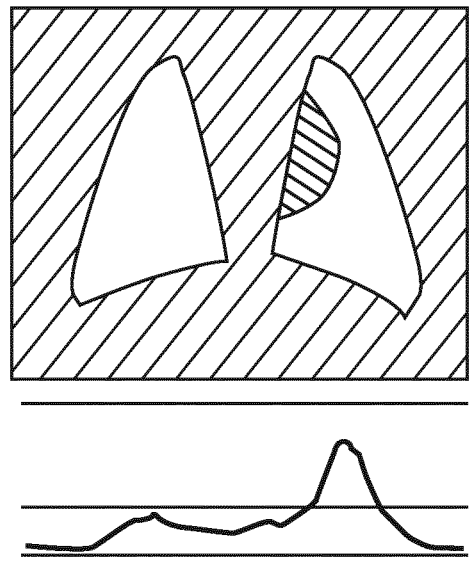
Fig. 6
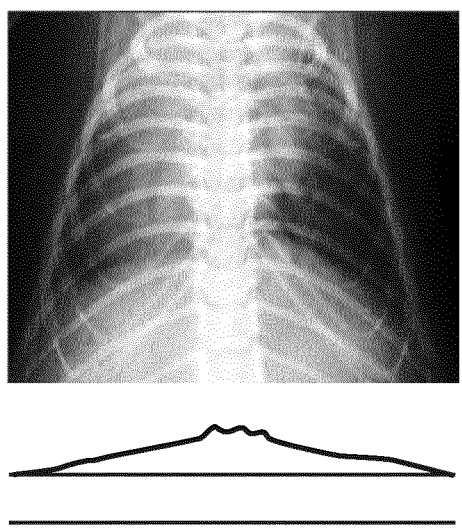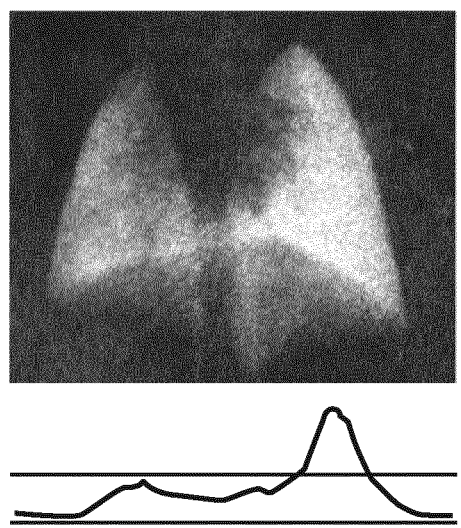
Fig. 7

APPARATUS FOR X-RAY IMAGING AN OBJECT

FIELD OF THE INVENTION

The present invention relates to an apparatus for X-ray imaging an object, and to a method for X-ray imaging an object, as well as to a computer program element and a computer readable medium.

BACKGROUND OF THE INVENTION

Grating-based differential phase contrast and dark-field imaging is promising technology that will likely add additional diagnostic value in particular in the area of chest imaging since the dark-field signal channel is highly sensitive to changes of the micro-structure of lung tissue.

US2012/0145912A1 describes a radiological image detection apparatus that includes a first grating, a second grating, a scanning unit, a radiological image detector, a radiation detection unit, and a control unit. The scanning unit relatively displaces at least one of the radiological image and the second grating to a plurality of relative positions at which phase differences of the radiological image and the second grating are different from each other. The radiation detection unit is provided on a path of the radiation and detects the radiation irradiated to the radiological image detector. The control unit allows the scanning unit to perform a relative displacement operation of the first grating and the second grating in a time period in which a radiation dose detection value of the radiation detected by the radiation detection unit is attenuated to a given level.

US 20151031986 A1 describes an x-ray equipment and the use of phase contrast imaging and focuses particularly on the properties of phase contrast image in respect of adjusting x-ray dose.

WO 20131004574 A1 (Jan. 1, 2013 OJ describes a method and equipment suitable for phase contrast imaging.

US 20131011040 A1 describes x-ray imaging using phase contrast imaging.

LIU YET AL: "Recent advances in synchrotron-based hard x-ray phase contrast imaging", JOURNAL OF PHYSICS D: APPLIED PHYSICS, INSTITUTE OF PHYSICS PUBLISHING LTD, GB, vol. 46, no. 49, 22 Nov. 2013 (2013-11-22), page 494001, XP020253615, ISSN: 0022-3727, DOI: 10.1088/0022-37271461491494001 discusses various work in the field of x-ray phase contrast imaging.

In pre-clinical studies, it has been demonstrated that wide-spread lung diseases like chronic obstructive pulmonary disease (COPD) and fibrosis can be accurately identified and even quantified by this technology. Still it remains open, how to build an operational system, such as a clinical system.

SUMMARY OF THE INVENTION

Therefore, it would be advantageous to have an improved apparatus for imaging an object.

The object of the present invention is solved with the subject matter of the independent claims, wherein further embodiments are incorporated in the dependent claims. It should be noted that the following described aspects of the invention apply also for the apparatus for X-ray imaging an object and the method for X-ray imaging an object, and for the computer program element and the computer readable medium.

According to a first aspect, there is provided an apparatus for X-ray imaging an object comprising:

an X-ray source;
an X-ray interferometer arrangement;
an X-ray detector; and
a processing unit.

The X-ray detector is configured to be positioned relative to the X-ray source such that at least a part of a region between the X-ray source and the X-ray detector is an examination region for accommodating an object. The X-ray detector is also configured to provide the processing unit with data relating to the detection of X-rays having at least partially passed through the X-ray interferometer arrangement. The X-ray interferometer arrangement is configured to be positioned between the X-ray source and the examination region or the X-ray detector and the examination region. The processing unit is configured to determine at least one transmission factor for the X-ray radiation transmitted through at least part of the object and configured to determine at least one dark-field factor for the X-ray radiation transmitted through at least part of the object. The processing unit is also configured to automatically control an intensity of X-ray radiation to be emitted towards the at least part of the object as a function of the determined at least one X-ray transmission factor and the determined at least one dark-field factor radiation. More precisely, the transmission factor is a factor indicating the overall attenuation of the X-ray by the object, or, put in other words, the fraction of intensity of X-ray radiation transmitted through the at least part of the object. More precisely, the dark field factor is a factor indicating the loss of fringe visibility caused by small angle scattering within the object, or, put in other words, the fraction by which the fringe visibility is reduced by the at least part of the object. The common model for the X-ray intensity measured at an X-ray detector when using a grating based interferometer is given by:

$$m(x)=TI_0(1+DV_0\cos(\phi+\phi_0+2\pi x/p))$$

wherein x is the position of the grating being stepped and p is the period of this grating; wherein $I_0$, $V_0$, and $\phi_0$ are respectively the intensity, the fringe visibility and the fringe phase for a measurement without and object; and wherein T, D, and $\phi$ characterize the modification of the fringe pattern by the object. Namely, T is the transmission factor (indicating the overall attenuation of the X-ray by the object); D is the dark-field factor (indicating a loss of fringe visibility caused by small angle scattering within the object), and $\phi$ is the phase shift of the fringe pattern caused by the object. Note that this is equivalent to another common formulation $$m(x)=I(1+V\cos(\phi+\phi_0+2\pi x/p))$$

where $I=TI_0$ and $V=DV_0$. Hence an estimation of the transmission factor T is equivalent to estimating the total transmitted intensity and an estimation of the dark-field factor D is equivalent to estimating the fringe visibility V with the object in the beam. In this manner, the apparatus can determine a transmission factor and a dark-field factor of radiation transmitted by an object, and the apparatus can in a control loop control the intensity of X-ray radiation to be emitted towards an object. In other words, data acquired with the system at a particular position can be used to determine optimal operation conditions at that position. In an example, the initial data used to determine the optimal operating conditions can be acquired with a low intensity of X-ray radiation and then at that scan arm position the intensity of X-ray radiation to be emitted towards the at least part of the object can be controlled for example by increasing the output of the X-ray source to the required level at that position. This enables the noise, and/or the signal to noise in an X-ray image (where "X-ray image" can be the attenuation image i.e. −log (T), the dark-field image i.e. −log (D), and/or the phase image i.e. ϕ) to be controlled as desired. For example, the noise and/or the signal to noise in a Dark field and/or phase contrast image can be controlled as desired by appropriately controlling the intensity of X-ray radiation to be emitted towards, and therefore potentially transmitted by, the object. To put it another way, the X-ray exposure of an object can be controlled such that the Dark field signal and/or phase contrast signal has a more homogeneous distribution across the image. In other words, automatic exposure control is provided for a DPCI apparatus, enabling automatic exposure control for phase contrast and/or dark field images. This means, for example for a living object such as a human the intensity of X-ray radiation can be optimised such that resultant images can be reviewed and interpreted effectively whilst minimising the radiation dose to the subject.

In an example, the apparatus comprises an output unit, wherein the output unit is configured to output data representative of the object.

In an example, the processing unit is configured to control the intensity of X-ray radiation to be emitted towards the at least part of the object as a monotonically decreasing function of the determined at least one dark-field factor.

In an example, the processing unit is configured to control the intensity of X-ray radiation to be emitted towards the at least part of the object as a monotonically decreasing function of the determined at least one transmission factor. In this manner, the transmission factor of X-ray radiation transmitted by an object and/or the X-ray dark-field factor can be determined in or from an X-ray image, and this information can be used to tune the acquisition parameters with respect to acquiring the next image. A control loop, i.e. feedback control, can then be implemented based on the X-rays transmission factor and/or dark-field factor In this manner, for example a low intensity of X-rays can be used to control the required intensity of X-rays to be used to provide the desired signal to noise, where the low intensity of X-rays is used to determine a transmission factor of X-rays and/or dark-field factor from which the required intensity of X-rays can be controlled in order to provide the required signal to noise across an image. In examples, this can be achieved through acquiring a pre-scan intensity X-ray image with the interferometer arrangement swung out of position, and/or controlled "on the fly" from data acquired with the interferometer arrangement in position, thereby enabling the X-ray intensity to be controlled (or adjusted) at each scan position.

In an example the processing unit is configured to determine the at least one X-ray fringe visibility as a function of the at least one transmission intensity of X-ray radiation, and the X-ray interferometer arrangement is positionable relative to the examination region such that X-rays detected by the X-ray detector have not all passed through the X-ray interferometer arrangement. In other words, on the fly determination of the dark-field factor can be used via an appropriate control loop to control the noise and/or signal to noise in the resultant X-ray image, such as a phase contrast or dark field image. The noise and/or signal to noise can be controlled to be at a predefined level for example being controlled such that the noise and/or signal to noise is substantially constant across an image. In other words, the at least one transmission factor can be determined making use of the apparatus operating in an interferometer mode. The determined at least one transmission factor radiation can then be used to determine the intensity of X-ray radiation to be emitted towards the at least part of the object, through for example a change in scan speed or a change in the operational characteristics of the X-ray source, in particular the tube current and/or the pulse duration. In other words, on the fly determination of the transmission factor of X-ray radiation can be used via an appropriate control loop to control the noise and/or signal to noise in the resultant X-ray image, such as a phase contrast or Dark field image. The noise and/or signal to noise can be controlled to be at a predefined level for example being controlled such that the noise and/or signal to noise is substantially constant across an image. In other words, the apparatus can be turned into a standard radiography apparatus and data acquired in this mode can be used for the determination of the transmission factor. Or put another way, the apparatus is configured in this arrangement to take a standard chest X-ray, and such a standard X-ray image can be used for the determination of the transmission factor. In other words, the influence of attenuation on the dark field signal and/or phase contrast image can be accounted for upfront, and it is not required to estimate this on the fly with the interferometer in position. Then, the determined transmission factor of radiation transmitted through the object with the interferometer swung out of position, in other words the knowledge about the attenuation, can be used with data acquired when the interferometer is swung back into position to make the on the fly determination of the dark field factor more accurate. A control loop can then be used to adjust the X-ray source or scan speed appropriately, on the basis of the determined transmission factor of X-ray radiation and determined dark field factor such that the intensity of X-ray radiation to be emitted towards the part of the object can be controlled as desired. This can be done in order that the noise and/or signal to noise ratio is constant or at a desired level or desired levels across the image.

In an example, the processing unit is configured to determine at least one transmission factor of X-ray radiation transmitted through a portion of the object, and wherein the processing unit is additionally configured to determine a region of interest within the portion of the object and wherein the at least one part of the object is the region of interest. In this manner, optimisation can be tuned to this region of interest. In other words, in an example an image (or scan) acquired with the interferometer arrangement swung out of position can be used to locate a particular region of importance (e.g., the lungs) and the apparatus enables the signal to noise over imagery of the lungs to be at a desired level. This enables faster acquisition of the required imagery because only those regions of importance need be scanned whilst controlling the intensity of X-ray radiation. In a similar manner, the interferometer can scan across the body, with for example a low intensity of X-ray radiation, to determine the location of the lungs and then a re-scan can be performed with the intensity of radiation being controlled such that the signal to noise across the imagery of the lungs is as desired. The intensity of radiation can be controlled through a change in the intensity of X-rays emitted by the source and/or a change in scan speed.

According to a second aspect, there is provided a method for X-ray imaging an object comprising:
a) providing data relating to the detection of X-rays, wherein an X-ray detector is configured to be positioned relative to an X-ray source such that at least a part of a region between the X-ray source and the X-ray detector is an examination region for accommodating an object, and wherein an X-ray interferometer arrangement is configured to be positioned between the X-ray source and the examination region or the X-ray detector and the examination region;

b) determining at least one X-ray dark-field factor for the X-ray radiation transmitted through at least part of the object;

c) determining at least one transmission factor for the X-ray radiation transmitted through at least part of the object; and d) automatically controlling an intensity of X-ray radiation to be emitted towards the at least part of the object as a function of the determined at least one dark-field factor and the determined at least one transmission factor of X-ray radiation.

In an example, the method comprises step e), the outputting of data representative of the object.

In an example, step d) comprises controlling the intensity of X-ray radiation to be emitted towards the at least part of the object as a function of the reciprocal of the determined at least one dark-field factor.

In an example, step d) comprises controlling the intensity of X-ray radiation to be emitted towards the at least part of the object as a monotonically decreasing function of the determined at least one transmission factor of X-ray radiation.

In an example, step d) comprises controlling the intensity of X-ray radiation to be emitted towards the at least part of the object as a function of the reciprocal of the determined at least one dark-field factor and controlling the intensity of X-ray radiation to be emitted towards the at least part of the object as a monotonically decreasing function of the determined at least one transmission factor of X-ray radiation.

In an example, step d) comprises controlling the intensity of X-ray radiation to be emitted towards the at least part of the object as a function of the reciprocal of the square root of the determined at least one transmission factor of X-ray radiation.

In an example, step b) comprises determining the at least one dark field factor, and positioning the X-ray interferometer arrangement relative to the examination region such that X-rays detected by the X-ray detector have passed through the X-ray interferometer arrangement.

In an example, step c) comprises determining at least one transmission factor, and positioning the X-ray interferometer arrangement relative to the examination region such that X-rays detected by the X-ray detector have passed through the X-ray interferometer arrangement.

In an example, step c) comprises determining the at least one transmission factor, and positioning the X-ray interferometer arrangement relative to the examination region such that X-rays detected by the X-ray detector have not all passed through the X-ray interferometer arrangement; and wherein step b) comprises determining the at least one dark field factor as a function of the at least one transmission factor.

Automatic exposure control is commonly used in x-ray radiography in order to ensure appropriate image quality without overdosing. In slot scan systems, automatic exposure control is dynamically adjusted to the local thickness of the patient. The advantage of the presently described aspects and examples is that automatic exposure control can be applied to a DPCI system with respect to dark-field and phase contrast imaging.

According to another aspect, there is provided a computer program element controlling apparatus as previously described which, in the computer program element is executed by processing unit, is adapted to perform the method steps as previously described.

According to another aspect, there is provided a computer readable medium having stored computer element as previously described.

Advantageously, the benefits provided by any of the above aspects and examples equally apply to all of the other aspects and examples and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings:

FIG. 1 shows an example of a method for X-ray imaging an object;

FIG. 2 shows a schematic set up of an example of an apparatus for X-ray imaging an object;

FIG. 6 shows a schematic representation of an experimental in-vivo mouse attenuation (absorption) image on the left and a schematic representation of the associated dark field image on the right, both acquired without exposure control. The bottom plot shows the dose profile during the scan that would generate a more homogeneous signal to noise ratio for each image.

FIG. 7 shows the same information is presented in FIG. 6, where the schematic representations are replaced by X-ray images.

DETAILED DESCRIPTION OF EMBODIMENTS

Figure 3:
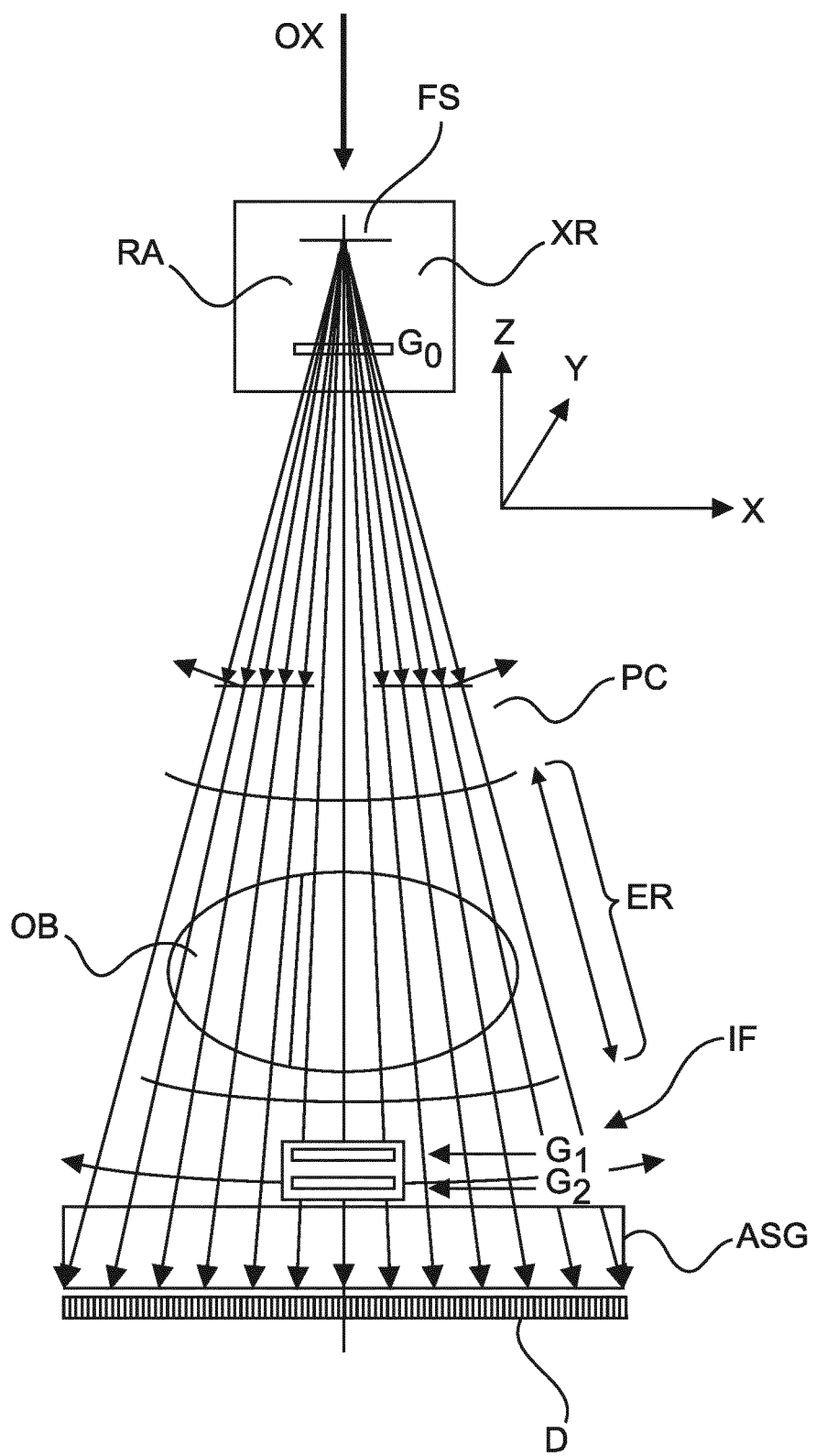
FIGS. 3-5 show schematic set ups of examples of an apparatus for X-ray imaging an object.

FIG. 1 shows a method 10 for X-ray imaging an object in its basic steps, where the outputting of data is optional. The method comprises the following:

In a providing step 20, also referred to as step a), data relating to the detection of X-rays is provided, wherein an X-ray detector is configured to be positioned relative to an X-ray source such that at least a part of a region between the X-ray source and the X-ray detector is an examination region for accommodating an object. An X-ray interferometer arrangement is configured to be positioned between the X-ray source and the examination region or the X-ray detector and the examination region.

In a first determining step 30, also referred to as step b), at least one X-ray dark-field factor is determined.

In a second determining step 40, also referred to as step c), at least one transmission factor of X-ray radiation transmitted through at least part of the object is determined.

In a controlling step 50, also referred to as step d), an intensity of X-ray radiation to be emitted towards the at least part of the object as a function of the determined at least one X-ray dark-field factor and the determined at least one transmission factor of X-ray radiation is controlled.

In an optional outputting step 60, also referred to as step e), data representative of the object is output.

According to an example, step d) comprises controlling 70 the intensity of X-ray radiation to be emitted towards the at least part of the object as a monotonically decreasing function of the determined at least one dark-field factor.

In an example, step d) comprises controlling the intensity of X-ray radiation to be emitted towards the at least part of the object as a function of the reciprocal of the determined at least one dark-field factor.

According to an example, step d) comprises controlling 80 the intensity of X-ray radiation to be emitted towards the at least part of the object as a monotonically decreasing function of the determined at least one transmission factor.

In an example, step d) comprises controlling the intensity of X-ray radiation to be emitted towards the at least part of the object as a function of the determined at least one transmission factor and more specifically as a function of the reciprocal of said determined at least one transmission factor.

According to an example, step d) comprises controlling 90 the intensity of X-ray radiation to be emitted towards the at least part of the object as a function of the square root of the determined at least one transmission factor T of X-ray radiation, and more specifically as a function of the reciprocal of said square root.

According to an example, wherein step b) comprises determining 100 the at least one dark field factor, and positioning the X-ray interferometer arrangement relative to the examination region such that X-rays detected by the X-ray detector have passed through the X-ray interferometer arrangement.

According to an example, step c) comprises determining the at least one transmission factor, and positioning the X-ray interferometer arrangement relative to the examination region such that X-rays detected by the X-ray detector have passed through the X-ray interferometer arrangement.

According to an example, step c) comprises determining 130 the at least one transmission factor, and positioning the X-ray interferometer arrangement relative to the examination region such that X-rays detected by the X-ray detector have not all passed through the X-ray interferometer arrangement; and wherein step b) comprises determining 120 the at least one dark field factor as a function of the at least one transmission factor.

In an example, the method comprises determining a region of interest of the object and the wherein the at least one part of the object is the region of interest.

In other words, in certain examples parts of step c) can occur before parts of step b), when this relates to acquiring an X-ray image in a standard radiography mode which can provide a mean transmitted intensity (intensity) of X-ray radiation and this can then be used when the apparatus is operating in the DPCI arrangement in order to determine a fringe visibility. In an example, the mean transmitted intensity (intensity) of X-ray radiation from the image acquired in the standard radiography mode can relate to a region of interest, such as the lungs of a patient, and then in the DPCI mode the visibility can be determined over the region of interest, from which with appropriate control feedback the required exposure can be determined in order that the noise and or signal to noise over the region of interest for an acquired dark field image or phase contrast image can be provided.

FIG. 2 shows an example of an apparatus 200 for X-ray imaging an object. The apparatus 200 comprises an X-ray source 210, an X-ray interferometer arrangement 220, an X-ray detector 230, and a processing unit 240. The X-ray detector 230 is configured to be positioned relative to the X-ray source 210 such that at least a part of a region between the X-ray source 210 and the X-ray detector 230 is an examination region for accommodating an object. The X-ray detector 230 is configured to provide the processing unit 240 with data relating to the detection of X-rays having at least partially passed through the X-ray interferometer arrangement. The X-ray interferometer arrangement 220 is configured to be positioned between the X-ray source and the examination region or the X-ray detector and the examination region. The processing unit 240 is configured to determine at least one dark field factor for X-ray radiation transmitted through at least part of the object, and configured to determine at least one transmission factor for X-ray radiation transmitted through at least part of the object. The processing unit 240 is configured to determine an intensity of X-ray radiation to be emitted towards the at least part of the object as a function of the determined at least one dark field factor and the determined at least one transmission factor.

In an example, the apparatus comprises an output unit 250 configured to output data representative of the object.

In an example, the apparatus is a differential phase contrast imaging (DPCI) apparatus. In an example, the apparatus generates an attenuation image, relating to the detection of intensity (intensity) values of X-rays with and without the object in the examination region. In an example, the apparatus generates a phase contrast (or differential phase) image, relating to the detection of the phases of the X-rays with and without the object in the examination region. In an example, the apparatus generates a dark field (or de-coherence) image, relating to the detection of fringe visibilities, i.e. the dark field factor, of the X-rays with and without the object in the examination region. In an example, the apparatus generates any combination of these images. For example, the apparatus can generate an attenuation image, and generate a phase contrast image, and generate a dark field image. In an example, an attenuation image, a phase contrast image, and a dark field image can be generated at the same time.

In an example, the interferometer arrangement comprises a Talbot interferometer. In an example, the interferometer arrangement comprises a diffraction grating configured to modulate onto the X-rays emitted by the source an interference pattern detectable by the X-ray detector as X-ray fringes from which the dark field factor is derived. In an example, the interferometer arrangement comprises a second diffraction grating configured to analyze the interference pattern. In an example, the second diffraction grating is an absorption grating. In an example, the two gratings are arranged on mutually opposite sides of the examination region. In an example, the two gratings are arranged on the same side of the examination region. In an example, the interferometer comprises a source grating in addition to the one or two gratings already discussed. In this example, the source grating is located relatively close to the X-ray source and serves to make the X-rays propagating after the source grating partly coherent. In other words, an X-ray source can be adapted so as to emit radiation that is more coherent than if the source grating was not present. Therefore, in some examples a source grating is not required, for example when the X-ray source already produces suitably coherent X-rays. In an example, the interferometer arrangement is configured to produce Moiré fringes. In an example, the interferometer arrangement is purposely detuned such that some fringes are present in the detector area. In an example, the interferometer arrangement is purposely detuned by having a first grating inclined at a small angle to a second grating. In an example, detuning leads to the generation of Moiré fringes on the detector.

In an example, the apparatus comprises a scanning arrangement. In an example, scanning comprises movement of the object through the examination region. In an example, scanning comprises movement of the object through the examination region whilst elements of the interferometer arrangement and/or X-ray source are stationary. In an example, scanning comprises movement of a grating with respect to the X-ray source. In an example, scanning comprises movement of the X-ray source whilst the object is stationary or is not intentionally being moved through the examination region and/or the X-ray source is stationary. In an example, scanning comprises movement of one grating with respect to a second grating. In an example, scanning comprises movement of the first grating and movement of a second grating such that the relative positions of the first grating to the second grating does not change. For example, the interferometer arrangement can be translated and/or rotated. In an example, scanning comprises movement of the X-ray source. In an example, scanning comprises movement of the X-ray source whilst elements of the interferometer arrangement are stationary. In other words, movement of the source, for example laterally, can lead to movement of the projection of the object image on the X-ray detector. For example, there can be a relative shift between the projection of the image and moiré fringes for particular example arrangements. In other words, the apparatus can be based on an adaptation of recently proposed scanning phase-contrast and/or dark field systems. However, the apparatus can be based on an adaptation of other scanning geometries, in particular the "classical" scanning geometry as implemented on the MicroDose system or in the geometry used by Kottler et al., where the object is moved through a stationary setup of tube, gratings and detector. The apparatus can also be based on an adaptation of full-field dark field and/or full field phase contrast systems.

In one example, the interferometer arrangement comprises two gratings which are fixedly mounted with respect to each other in a suitable frame or cage and this frame is fixedly arranged in a scan arm or other moveable gantry structure. In other words, the interferometer arrangement can be swung in and out of the X-ray beam such that the apparatus can be operated in both a DPCI mode and in a conventional radiography mode. In the DPCI mode, the arm can be translated or rotated, such that the at least part of the body is scanned.

In an example, the apparatus comprises a slot scan arrangement. In an example, the X-ray source is configured to emit different intensities of X-rays. In an example, a relatively large X-ray detector (possibly a full field X-ray detector) is used in combination with a relatively small (that is, compared to the field of view of the X-ray detector) interferometer arrangement. In this example, the interferometer arrangement during an imaging operation can be moved by the apparatus across the field of view for scanning purposes. In this manner, because the detector pixels are not moving during the imaging operation, the effects of motion blur are reduced and a less expensive detector than may otherwise be required to suppress image blur can be used.

In an example, the processing unit being configured to control an intensity of X-ray radiation to be emitted towards the at least part of the object comprises controlling an intensity of X-rays to be emitted by the X-ray source as a function of the determined at least one dark field factor and as a function of the determined at least one transmission factor. In an example, the X-ray source comprises an X-ray tube and the processing unit being configured to control an intensity of X-rays to be emitted by the X-ray source results in appropriately modulating the tube current during a scan. For example, the tube current can be appropriately modulated to increase or decrease the intensity of X-rays emitted by the X-ray source. In an example, the tube current is modulated and the scan speed is changed.

In an example, the processing unit—being configured to control an intensity of X-ray radiation to be emitted towards the at least part of the object—is also configured for controlling a scan speed. For example, an increase in scan speed can lead to a decrease in the intensity of X-ray radiation emitted towards a part of the body, because X-rays can propagate through the body part for a decreased period of time. In other words, the X-ray flux directed towards, and which can potentially pass through, the body part is reduced.

In an example, the output unit is configured to output data representative of the transmission factor.

In an example, the output unit outputs an absorption (or attenuation) image. In an example, the output unit outputs a phase contrast (or differential phase) image. In an example, the output unit outputs a dark field image. In an example, the output unit outputs any combination of attenuation, phase contrast and dark field images. In other words, the output unit can simultaneously output all three types of image. In an example, the output unit outputs data representative of the object on a monitor such as a visual display unit or on a number of separate monitors. For example, attenuation, phase contrast and dark field images can be presented on a single monitor or presented on separate monitors.

The skilled person will appreciate that a unit such as a signal estimation unit can be used to determine at least one dark field factor and the at least one transmission factor. The skilled person will also appreciate that an exposure control unit can control an intensity of X-ray radiation to be emitted towards the at least part of the object as a function of the determined at least one dark field factor and the determined at least one transmission factor. It is specified that a processing unit carries out these tasks, however this could be carried out by separate units as would be appreciated by the skilled person.

In an example, the apparatus has useful application in a clinical environment such as a hospital. In an example, the apparatus can be used for mammography, diagnostic radiology and interventional radiology for the medical examination of patients. In an example, the apparatus has useful application in an industrial environment, for example in non-destructive testing (e.g. analysis as to composition, structure and/or qualities of biological as well non-biological samples) as well as security scanning (e.g. scanning of luggage in airports).

According to an example, the processing unit is configured to control the intensity of X-ray radiation to be emitted towards the at least part of the object as a monotonically decreasing function of the determined at least one dark field factor.

According to an example, the processing unit is configured to control the intensity of X-ray radiation to be emitted towards the at least part of the object as a monotonically decreasing function of the determined at least one transmission factor.

In an example, the processing unit is configured to control the intensity of X-ray radiation to be emitted towards the at least part of the object as a strictly monotonically decreasing function of the determined at least one dark field factor, and/or is configured to control the intensity of X-ray radiation to be emitted towards the at least part of the object as a strictly monotonically decreasing function of the determined at least one transmission factor. In an example, the processing unit is configured to control the intensity of X-ray radiation to be emitted towards the at least part of the object as being proportional to the reciprocal of the determined at least one dark field factor, and/or is configured to control the intensity of X-ray radiation to be emitted towards the at least part of the object as being proportional to the reciprocal of the determined at least one transmission factor.

In an example, the processing unit is configured to control the scan speed as a function of the reciprocal of the determined at least one dark field factor, and/or is configured to control the scan speed as a function of the reciprocal of the determined at least one transmission factor.

In other words, the apparatus makes use of the fact that image noise in a DPCI apparatus, for differential phase contrast imaging and dark field imaging, scales inversely with fringe visibility i.e. dark field factor and transmitted X-ray intensity (or intensity) i.e. transmission factor. Or to put this another way, automatic exposure control is provided that controls exposure based on an expected or desired noise and/or signal to noise level in a dark field and/or phase contrast image.

In an example, the processing unit is configured to control the intensity of X-ray radiation to be emitted towards the at least part of the object as being proportional to the reciprocal of the square root of the determined at least one factor.

In an example, the processing unit is configured to control the scan speed as a function of proportional to the reciprocal of the square root of the determined transmission factor.

In an example, the fringe pattern generated at a current scan arm position i.e. the dark field factor for such scan arm position is used to determine a visibility or mean visibility at that arm position. The determined visibility can then be used to control the intensity of X-ray radiation to be emitted towards the at least part of the object, through for example a change in scan speed or a change in the operational characteristics of the X-ray source.

According to an example, the processing unit is configured to determine the at least one transmission factor, and to position the X-ray interferometer arrangement relative to the examination region such that X-rays detected by the X-ray detector have passed through the X-ray interferometer arrangement.

In an example, the fringe pattern generated at a current scan arm position is used to determine a transmission factor of X-ray radiation at that arm position. DCPI processing of the acquired fringe pattern can be used to determine the transmission factor of X-ray radiation.

In an example, the fringe pattern generated at a current scan arm position is used to determine a dark-field factor or mean dark-field factor and at the same time is used to determine a transmission factor of X-ray radiation at that arm position. The determined dark-field factor and determined transmission factor can then be used to control the intensity of X-ray radiation to be emitted towards the at least part of the object, through for example a change in scan speed or a change in the operational characteristics of the X-ray source. In other words, on-the-fly determination of the dark-field factor and transmission factor of X-ray radiation can be used via an appropriate control loop to control the noise and/or signal to noise in the resultant X-ray image, such as a phase contrast or Dark field image.

In an example, rather than use the fringe pattern generated at a current scan arm position is to determine a transmission factor of X-ray radiation at that arm position the total flux of radiation transmitted by the part of the object is measured and this is used to determine the transmission factor of X-ray radiation. In other words, the total flux across the fringe pattern is measured, and DPCI processing based on the fringe pattern need not be used. In an example, DPCI processing and the total flux can be used to determine the transmission factor of X-ray radiation.

According to an example, the processing unit is configured to position the X-ray interferometer arrangement relative to the examination region such that X-rays detected by the X-ray detector have not all passed through the X-ray interferometer arrangement, and to determine the at least one dark field factor as a function of the at least one transmission factor.

In other words, parts of the interferometer arrangement can be swung out of position in order that the apparatus is in effect operating in the manner of a conventional X-ray apparatus. However, the skilled person will appreciate that parts of the interferometer arrangement could remain in place, such as a source grating for collimation of the X-ray beam, but with the other gratings swung out of position the apparatus is not then operating as an interferometer.

In an example, the processing unit is configured to determine the dark field factor when the X-ray interferometer arrangement is positioned relative to the examination region such that X-rays detected by the X-ray detector have not passed through any part of the X-ray interferometer arrangement. In an example, a first grating is used to form a (more) coherent beam and the first grating is kept in place whilst other parts of the interferometer arrangement are swung out of the beam. For example, the gratings used to generate Moiré fringes may be swung out of the X-ray beam, but the source grating used to generate a more coherent source of radiation may remain in place.

In an example, a standard radiograph image acquired with the X-ray interferometer swung out of position is used to determine a mean transmission intensity (transmitted intensity) of the part of the object. In this example, the X-ray interferometer is then swung back into position such that X-ray radiation passes through it and data is acquired over the part of the object. The mean transmission intensity (transmitted intensity), acquired without the interferometer, can be used with data acquired with the interferometer to determine a mean visibility over the part of the object. The determined transmission intensity of X-ray radiation and the determined visibility can then be used to control the intensity of X-ray radiation to be emitted toward the at least part of the object, through for example a change in scan speed or a change in the operational characteristics of the X-ray source. In other words, a standard X-ray image can be used to adjust or tailor the exposure control even further.

In an example, prior to acquisition of X-ray image data using a DPCI system, the interferometer can be swung out of the X-ray beam and a standard X-ray image acquired. In other words, in an example a state-of-the-art X-ray image can be acquired with X-ray tube voltage and focal spot size selected for optimal image quality of a transmission image. In an example, segmentation of the acquired standard image can provide the position of a region of interest, e.g. lung, where a constant (desired) noise level and/or constant (desired) signal to noise level is required. Then, the transmission factor can be determined.

According to an example, the processing unit is configured to determine a region of interest of the object and the wherein the at least one part of the object is the region of interest.

In an example, the processing unit is configured for determining the region of interest when the X-ray interferometer arrangement is positioned relative to the examination region such that X-rays detected by the X-ray detector have passed through the X-ray interferometer arrangement. In other words, the region of interest can be determined on the fly.

In an example, the processing unit is configured for determining the region of interest when the X-ray interferometer arrangement is positioned relative to the examination region such that X-rays detected by the X-ray detector have not passed through the X-ray interferometer arrangement. In other words, the region of interest can be determined from a standard X-ray image.

FIG. 3 shows an apparatus for X-ray imaging an object, providing more detail on how the attenuation, phase contrast and dark field images are acquired. The apparatus is capable of imaging for the spatial distribution of absorption of, or in, an object OB and also capable of imaging for the spatial distribution of refraction (phase contrast imaging) and also capable of imaging for the spatial distribution of small angle scattering (dark field imaging). The apparatus has a grating based interferometer IF that can be scanned across a stationary X-ray detector D. In this example, the interferometer IF comprises two grating structures G1 and G2 although, although in other examples a single grating interferometer (having only a single grating G1) is used. In the specific case of a single grating interferometer IF, the X-ray detector D has a pitch sufficiently small, hence a spatial resolution sufficiently large, for detecting i.e. adequately resolving the interference pattern generated by the grating G1 for the purpose of differential phase contrast imaging and/or dark field imaging. For that purpose the X-ray detector may be a high resolution X-ray detector, having for example a spatial resolution of 50 micrometers or more.

In FIG. 3, the grating G1 is either an absorption grating or phase shift grating whereas G2 is an absorption gating. The gratings are manufactured by photo lithographically processing suitable substrates such as a silicon wafer. A pattern of periodic rulings is formed in those silicon "cards" formed by trenches of different aspect ratio. The ruling patterns may be one dimensional but may also be two dimensional such as to confer a checker board pattern.

The X-ray imaging apparatus further comprises an X-ray source XR and the X-ray detector D. The X-ray detector D can be a 2D full view X-ray detector, which is either planar or curved. A plurality of detector pixels are arranged in rows and columns as an array to form a 2D X-ray radiation sensitive surface capable of registering X-ray radiation emitted by the X-ray source.

The X-ray detector D and the X-ray source are spaced apart to form an examination region ER. The examination region is suitably spaced to receive the object OB to be imaged. The object may be inanimate or animate. For instance the object may be a piece of luggage or other sample to be imaged, or in a medical context the object may be a human or animal patient or at least an anatomic part of a human or animal.

The interferometric grating structures G1 and G2 are arranged in the examination region ER between the X-ray source XR and X-ray detector D. The X-ray source XR has a focal spot FS from which the X-ray radiation beam emerges. It is the space between the focal spot FS and the X-ray detector's radiation sensitive surface where the two or three grating structures are arranged. The grating G1 is a phase grating and the grating G2 is an analyzer grating. In some embodiments, there is in addition to the interferometric gratings G1, G2 of the interferometer IF, a further grating G0 which is the source grating.

The source grating G0 is arranged in proximity of the X-ray source, for example at the exit window of a housing of the X-ray tube. The function of the source grating G0 is to make the emitted radiation at least partly coherent. In other words, the source grating G0 can be dispensed with if an X-ray source is used which is capable of producing coherent radiation.

In operation the at least partly coherent radiation passes through the examination region ER and interacts with the object OB. The object then modulates the attenuation, refraction, and small angle scattering information onto the radiation which can then be extracted by operation of the grating tandem G1 and G2. The gratings G1, G2 induce an interference pattern which can be detected at the X-ray detector D as fringes of a Moiré pattern. If there was no object in the examination region, there would still be an interference patter observable at the X-ray detector D, called the reference pattern which is normally captured during a calibration procedure. This comes about by especially adjusting or "de-tuning" the mutual spatial relationship between the two gratings G1 and G2 by inducing a slight flexure for instance so that the two gratings are not perfectly parallel. Now, if the object is positioned in the examination region and interacts with the radiation as mentioned, the Moiré pattern, which is now more appropriately called the object pattern, can be understood as a disturbed version of the reference pattern. This difference from the reference pattern can then be used to compute one or all of the three images (attenuation, phase contrast, dark field). To be able to acquire suitable signals from which the images can be computed, a scanning motion is performed by the grating tandem G1-G2. As a result of this motion, at each pixel of the X-ray detector D a series of intensity values are detected. For good results, the detuning of the gratings G1, G2 is such that a period of the Moiré pattern should extend for a few of its cycles (two or three) in the direction of the scan motion. For each X-ray detector pixel, the series of intensity values can then be fitted to a (sinusoidal) signal forward model, for example, in order to derive the respective contributions of refraction, absorption, and small angle scatter. This type of signal processing is done in a signal processing unit not shown in FIG. 3, but which is known to the skilled person. The X-ray detector D remains stationary for any given orientation of the optical axis OX which is shown in FIG. 3 to extend along the Z axis. In other words, the X-ray detector D is kept stationary (at least during an image acquisition operation) with respect to an arbitrary reference point in the examination region. The interferometric setup as described above is what is commonly referred to as a Talbot-Lau interferometer. The distances between G0 and G1 and between G1 and G2 must be finely tuned to fit the requirements of Talbot distance which in turn is a function of the "pitch" (that is, the spatial period of the grating rulings) of the respective grating. Moving the interferometer IF relative to the X-ray detector D may cause a slight change in fringe distribution due to fringe drift. However, the fringe drift can be compensated by relating such drift to the fringe drift as obtained with a reference scan. Such reference scan may be a blank scan performed at the installation of the X-ray imaging apparatus.

The interferometer IF can be essentially a "grating pack" with the two gratings G1 and G2 fixedly mounted with respect to each other in a suitable frame or cage and this frame is fixedly arranged in a scan arm GT or other moveable gantry structure (not shown in FIG. 3). The arm, and with it the interferometer IF performs a pendulum like motion across the X-ray detector surface. The pivot point for the scan arm motion runs through the focal spot FS of the X-ray source but does not need to. The gratings G1 and G2 of the interferometer IF are held in fixed spatial relationship with respect to each other at all times during the scan motion and remain essentially parallel, or at least in a fixed spatial relationship, to G0. Suitable tracking circuitry (not shown) correlates interferometer position with X-ray detector pixel position to timely trigger a sequence of read-out burst to make sure each pixel is supplied with the above mentioned series of measurements to correctly sample the interference pattern.

In FIG. 3, the X-Y plane is the X-ray detector plane with X,Y designating the direction of pixelation in the X-ray detector D. The X-ray source rotates around the focal point that passes through the focal spot FS. The rotation axis RA for the scan arm GT and X-ray source XR extends into the paper plane of FIG. 3 (along the Y direction). Having the X-ray source rotate in concert with the pendulum motion of the grating tandem G1, G2 allows increasing flux.

In the example of FIG. 3, a pre-collimator is arranged between the X-ray source and the object OB so as to conform the radiation beam to the dimensions or footprint of the gratings G1 and/or G2. The collimator PC moves in concert with the pendulum motion of the interferometer IF during the image acquisition. One way to achieve this is to mount the collimator to the scan arm GT proximate to the source grating G0 at an appropriate distance. The source grating G0 also moves in concert with the swinging scanning motion of the grating pack G1, G2. One way to do this, is to mount the grating in the scan arm. An anti-scatter grid ASG may be arranged between the interferometer and the X-ray detector surface.

In the example of FIG. 3 it is envisaged that the object, e.g. a patient, OB lies on an examination table or couch (not shown in FIG. 3) during the image acquisition. In other words the patient's longitudinal axis extends into the drawing plane as per FIG. 3 whilst the pendulum motion of the gratings G1, G2 (and that of G0) swings in a vertical plane with the patient's longitudinal axis (in FIG. 3 extending into the Y direction) extending into the paper plane of FIG. 3.

The mutually rigidly mounted gratings G1, G2 move the full length from one X-ray detector edge to the opposing X-ray detector edge if a full field image is desired, i.e. an image that is as wide in scan direction as the X-ray detector itself. If the user requests a smaller FOV (field of view), however, a reduced scan range can be used to minimize the acquisition time.

Figure 4:
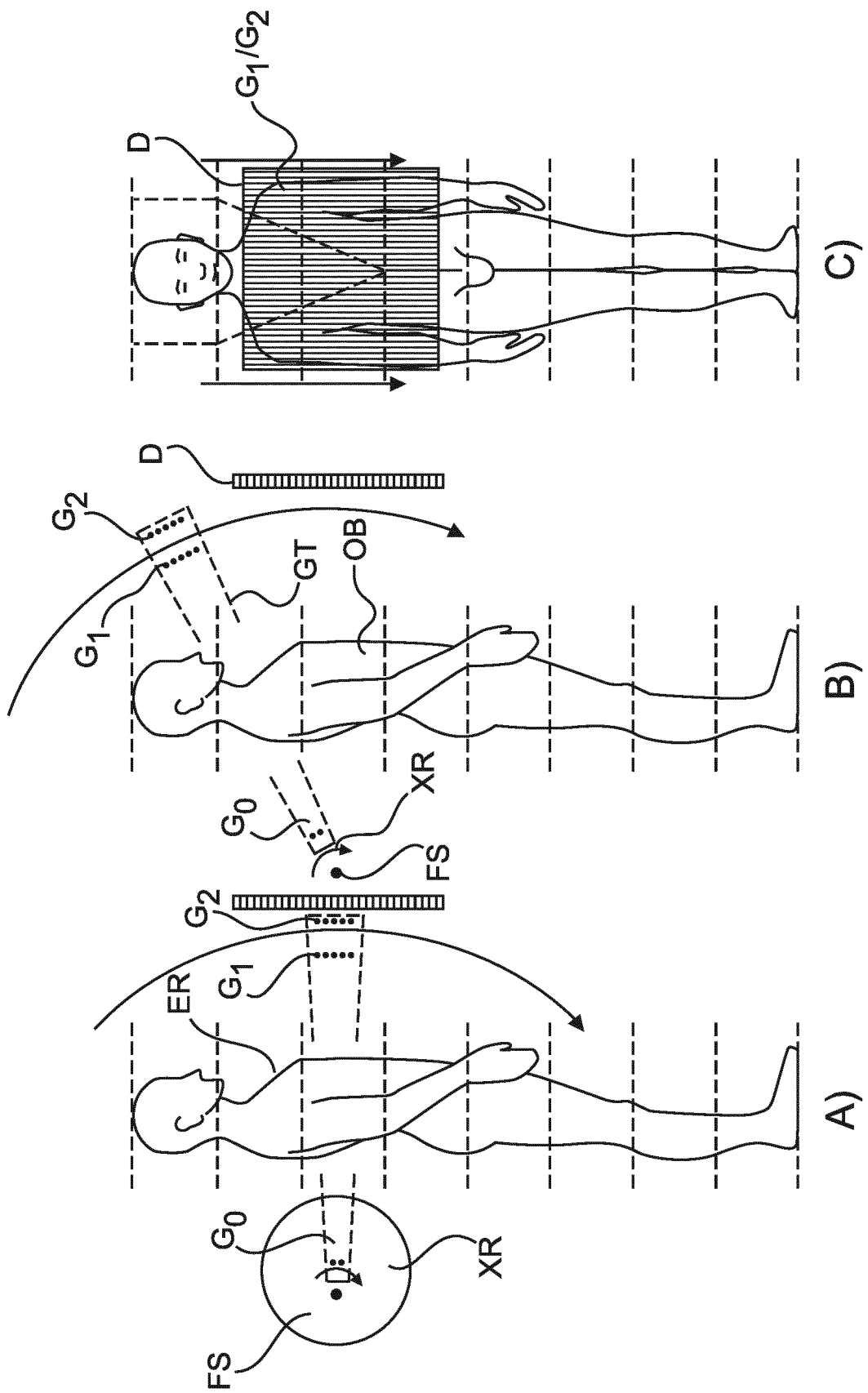

FIG. 4 shows a different example configured to allow the patient to stand (upright) during the X-ray imaging acquisition. This construction may be beneficial for chest imaging. Views A, B represent side elevations of the arrangement whilst view C is a frontal view through the X-ray detector D towards the X-ray source XR, that is, along the optical axis OX. Compared to FIG. 3 the optical axis in the FIG. 4 example is effectively rotated by 90 degrees. In other words the interferometer IF now performs a curved scan motion in a vertical direction (relative to the ground of the examination room) from top to bottom or from bottom to top. This is indicated in frontal view C by the arrows showing a (downward) movement of the interferometer IF during operation. Although not necessarily so in all examples, in FIG. 4 the gratings G1, G2 of the interferometer IF are now essentially arranged as strip gratings that are co-extensive of the width of the X-ray detector perpendicular to the scanning motion. Again gratings G1, G2 may be formed monolithically from single long wafer or substrate. However, in other embodiments, the strip arrangement can be achieved by tiling, that is joining together a plurality of smaller individual monolithic grating modules. The X-ray detector may be suspended in a fixture from the ceiling of the examination room or may be mounted on a floor mounted stand. The gratings G1 and G2 are rigidly mounted to a scan arm GT. Equally, the scan arm GT may be floor or ceiling mounted. The side views A) and B) show different instances during the scanning motion of the scan arm GT as it is moving along the vertical scan path in a circular or at least arcuate motion. Again, although not necessarily in all embodiments, the source grating G1 is arranged to rotate in concert about the focal spot FS. One way to do this is to have all three gratings arranged in the scan arm to maintain a fixed and parallel relationship during the vertical up or down motion. In FIG. 4 parts that move simultaneously or in concert are shown in the dashed box representing the scan arm GT.

Figure 5:
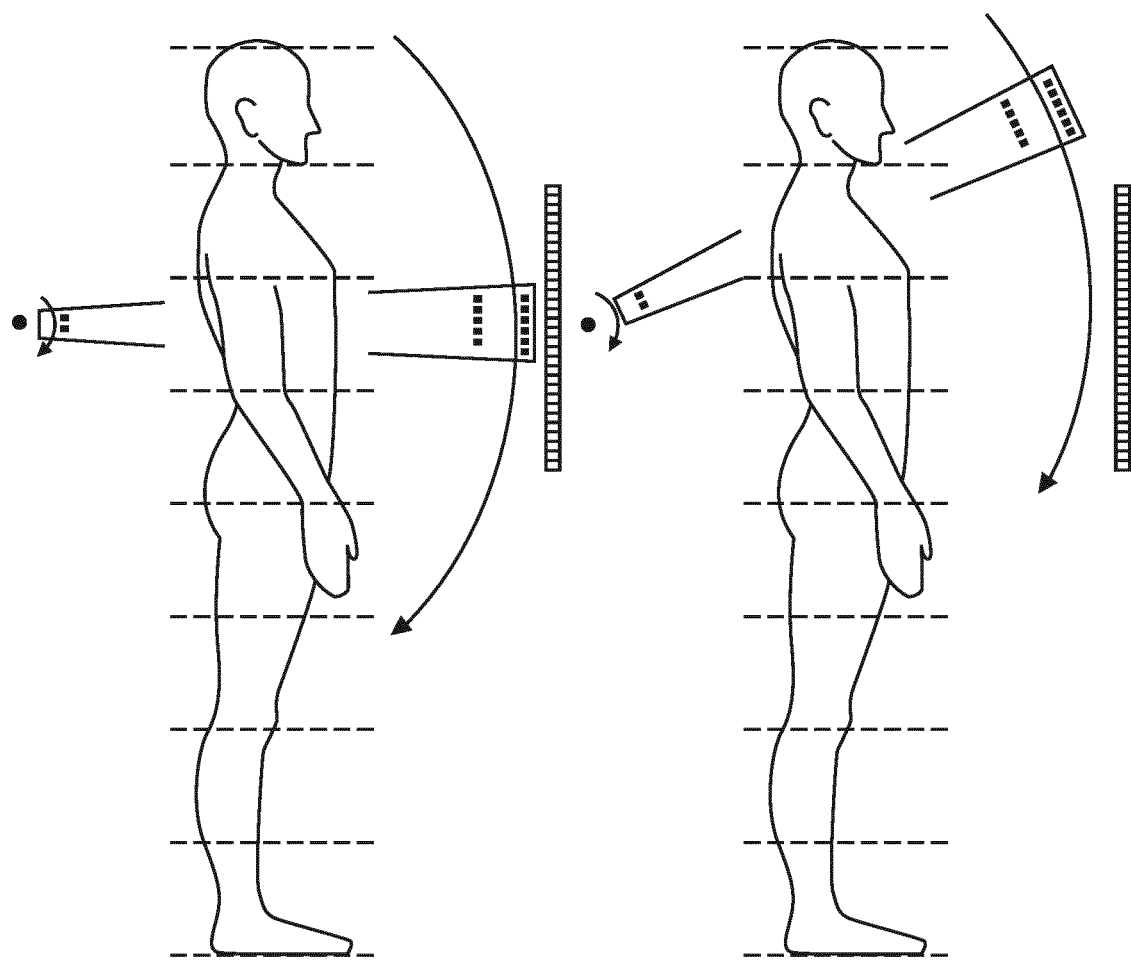

FIG. 5 shows an example of an X-ray imaging apparatus. A full field detector is used in combination with a small interferometer, which scans across the detector area the interferometer creates a fringe pattern that moves during the scan over the detector. The system can easily be operated in the conventional radiography mode by simply moving the scan arm with the gratings out of the beam. The grey boxes indicate that the components within the box move simultaneously. The right image shows the scan arm position just before the phase contrast and dark field scan starts, where all gratings are outside the beam. In this position, a standard chest X-ray image can be taken. Here, a top down motion is illustrated, but in other examples the scan arm can move differently for example in a left right direction. In other words, the X-ray imaging apparatus can easily be operated in the conventional radiography mode by simply moving the scan arm with the gratings out of the beam.

In an example, the mechanism for exposure control can be further explained as follows. Relating to the noise in the dark field image or phase contrast image, the following relation approximately holds:

$$\sigma \propto \frac{1}{DV_0\sqrt{TI_0}}$$

where $\sigma$ is the noise, $I_0$ is the intensity of X-ray radiation to be emitted towards the at least part of the object, T is the transmission factor, $V_0$ is the fringe visibility without the object, and D is the dark field factor. Note that in a scanning dark-field and phase contrast system, in other words in the DPCI arrangement, the interferometer is purposely detuned such that some fringes are present on the detector area. This fringe pattern can be used to estimate roughly on the fly a mean visibility at the current scan arm position. At the same time, the total flux can be measured so that a rough estimate for the noise in the dark-field image can be obtained based on the above equation. This noise estimate can be used to control the exposure (i.e., $I_0$ in the noise relation) to achieve a more homogenous dark-field image and phase contrast image. In other words, during the scan the dark field factor D and transmission factor T can be determined, and then used with a control loop to modify the exposure level at that scan arm position. By doing this, a required noise level or signal-to-noise level across the image can be provided.

Furthermore, the fact that the scanning system as shown in FIGS. 3-5 can acquire a standard chest X-ray image immediately before the scan can be exploited (a standard chest X-ray can be taken at any time, by simply swinging the scan arm out of position). A standard chest X-ray image can provide a state-of-the-art X-ray image with tube voltage and focal spot size selected for optimal image quality of the transmission image. This image can be used to tailor the exposure control even further, as now described. First, a quick segmentation of the image can provide the position of the lung, i.e., the area of interest where a constant noise-level in the dark-field image is desired (however, it is to be noted that such determination of an area of interest can be made during an image scan with the scan arm in position). Secondly, the influence of the attenuation on the dark-field noise level and phase contrast noise level can be accounted for upfront, i.e., it is not required to estimate this signal component on the fly. Finally, the knowledge about the attenuation makes the on-the-fly estimation of the visibility more accurate.

A specific estimate for the dark field factor can be obtained as following reasoning:

At a certain scan arm position, a detector readout is performed providing some measurements:

$$m_i = T_i I_i [1 + D_i V_i \cos(\phi_i - \phi_i^{(0)})]$$

where i indexes all pixels, and $\phi$ and $\phi^{(0)}$ are the fringe phase shift induced by the object and the blank scan phase of the fringes, and where $I_i$ is the intensity of X-ray radiation to be emitted towards the i-th pixel, and $V_i$ is the fringe visibility without the object and $D_i$ and $T_i$ are the dark-field and transmission factors for the i-th pixel. The upfront x-ray image, i.e. the standard X-ray image with the scan arm swung out of position, provides an estimate for the mean transmitted intensity, which is denoted by $\hat{I}_i$. Thus, rearrangement of the above equation provides:

$$D_i \cos(\phi_i - \phi_i^{(0)}) \approx \frac{m_i - \hat{I}_i}{V_i \hat{I}_i}$$

Since a relatively high-frequency fringe pattern is used in the scanning system, it can be safely assumed that $\phi_i - \phi_i^{(0)}$ is uniformly distributed over 360° and the square of the cosine term will be on average ½. Thus, applying this to the above equation an estimate for the mean visibility $\hat{D}$ for the detector readout can be obtained by:

$$\hat{D}^2 \approx \frac{2}{N} \sum_{i=1}^{N} \left( \frac{m_i - \hat{I}_i}{V_i \hat{I}_i} \right)^2$$

In other words, measurements taken with the DPCI system, with X-ray radiation passing through the interferometer arrangement, can make use of a previously acquired standard X-ray image where the scan arm was swung out of position. The mean dark field factor and mean transmission factor can be used to forecast the noise in the image, enabling control feedback to appropriately modify the intensity of X-rays passing through the object. This can be done by modifying the output of the X-ray source, and/or changing the scan rate.

The lung segmentation on the initial x-ray image can be easily included by summing in this equation only over image pixels inside the lung.

FIG. 6 and FIG. 7 shows a schematic representation of an experimental in-vivo mouse attenuation (absorption) image on the left and a schematic representation of the associated dark field image on the right, both acquired without exposure control. Applying the procedure for determining automatic exposure control, the bottom plot shows a dose profile during the scan that would generate a more homogeneous signal to noise ratio. Left: For a homogeneous noise level in the attenuation, the dose must be high for large attenuation, e.g. for imaging the spine. Right: For a homogeneous noise level in the dark-filed image, the dose must be high for strong dark field contrast (lungs, in particular the left lung shown on the right side). This highlights that automatic exposure control, as presently used for standard x-rays as represented by the plot on the left, is not appropriate for also providing a homogeneous noise or signal-to-noise level in a phase contrast or dark-field image. However, the automatic exposure control described here enables improved phase contrast and dark-field images to be acquired, where noise and or signal-to-noise is as required across the imagery.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A method for X-ray imaging an object, comprising:
providing data relating to the detection of X-rays, wherein an X-ray detector is configured to be positioned relative to an X-ray source such that at least a part of a region between the X-ray source and the X-ray detector is an examination region for accommodating an object, and wherein an X-ray interferometer is configured to be positioned between the X-ray source and the examination region or the X-ray detector and the examination region;
determining at least one dark field factor for the X-ray radiation transmitted through at least part of the object;
determining at least one transmission factor for the X-ray radiation transmitted through at least part of the object; and
automatically controlling an intensity of X-ray radiation to be emitted towards the at least part of the object as a function of the determined at least one dark field factor and the determined at least one transmission factor.

2. The method according to claim 1, further comprising controlling the intensity of X-ray radiation to be emitted towards the at least part of the object as a monotonically decreasing function of the determined at least one dark field factor, and/or controlling the intensity of X-ray radiation to be emitted toward the at least part of the object as a monotonically decreasing function of the determined at least one transmission factor.

3. The method according to claim 1, further comprising controlling the intensity of X-ray radiation to be emitted towards the at least part of the object as a function of the reciprocal of the square root of the determined at least one transmission factor.

4. The method according to claim 1, further comprising determining the at least one transmission factor, and positioning the X-ray interferometer relative to the examination region such that X-rays detected by the X-ray detector have not all passed through the X-ray interferometer arrangement; and determining at least one dark field factor as a function of the at least one transmission factor.

5. The method according to claim 1, wherein the at least one transmission factor is a fraction of intensity of the X-ray radiation transmitted through the at least part of the object.

6. The method according to claim 1, wherein the at least one dark field factor is a fraction by which a fringe visibility is reduced by the at least part of the object.

7. An apparatus for X-ray imaging an object, comprising:
an X-ray detector configured to be positioned relative to an X-ray source such that at least a part of a region between the X-ray source and the X-ray detector is an examination region for accommodating the object, the X-ray detector being configured to provide data relating to detection of X-rays having at least partially passed through an X-ray interferometer, wherein the X-ray interferometer is configured to be positioned between the X-ray source and the examination region or the X-ray detector and the examination region; and
a processor configured to determine at least one transmission factor for the X-ray radiation transmitted through at least part of the object, the processor being configured to determine at least one dark field factor for the X-ray radiation transmitted through at least part of the object, the processor being configured to automatically control an intensity of X-ray radiation to be emitted towards the at least part of the object as a function of the determined at least one transmission factor and the determined at least one dark field factor.

8. The apparatus according to claim 7, wherein the processor is configured to control the intensity of X-ray radiation to be emitted towards the at least part of the object as a monotonically decreasing function of the determined at least one dark field factor.

9. The apparatus according to claim 7, wherein the processor is configured to control the intensity of X-ray radiation to be emitted towards the at least part of the object as a monotonically decreasing function of the determined at least one transmission factor.

10. The apparatus according to claim 7, wherein the X-ray interferometer is positionable relative to the examination region such that X-rays detected by the X-ray detector have not all passed through the X-ray interferometer; and wherein the processor is configured to determine the at least one dark field factor as a function of the at least one transmission factor.

11. The apparatus according to claim 7, wherein the processor is configured to determine a region of interest within the portion of the object, and the wherein the at least one part of the object is the region of interest.

12. The apparatus according to claim 7, wherein the at least one transmission factor is a fraction of intensity of the X-ray radiation transmitted through the at least part of the object.

13. The apparatus according to claim 7, wherein the at least one dark field factor is a fraction by which a fringe visibility is reduced by the at least part of the object.

14. A non-transitory computer-readable medium having one or more executable instructions stored thereon, which when executed by a processor, cause the processor to perform a method for X-ray imaging an object, the method comprising:
providing data relating to the detection of X-rays, wherein an X-ray detector is configured to be positioned relative to an X-ray source such that at least a part of a region between the X-ray source and the X-ray detector is an examination region for accommodating an object, and wherein an X-ray interferometer is configured to be positioned between the X-ray source and the examination region or the X-ray detector and the examination region;

determining at least one dark field factor for the X-ray radiation transmitted through at least part of the object;
determining at least one transmission factor for the X-ray radiation transmitted through at least part of the object; and
automatically controlling an intensity of X-ray radiation to be emitted towards the at least part of the object as a function of the determined at least one dark field factor and the determined at least one transmission factor.

* * * * *